United States Patent [19]

Hartley

[11] Patent Number: 5,035,996

[45] Date of Patent: Jul. 30, 1991

[54] PROCESS FOR CONTROLLING CONTAMINATION OF NUCLEIC ACID AMPLIFICATION REACTIONS

[75] Inventor: James L. Hartley, Frederick, Md.

[73] Assignee: Life Technologies, Inc., Gaithersburg, Md.

[21] Appl. No.: 360,120

[22] Filed: Jun. 1, 1989

[51] Int. Cl.$^5$ .............. C12Q 1/68; C12P 19/34; C12N 9/22; C12N 9/78

[52] U.S. Cl. .......................... 435/6; 435/91; 435/200; 435/227

[58] Field of Search ............... 435/6, 91, 227, 200; 536/21

[56] References Cited

U.S. PATENT DOCUMENTS 4,683,202  7/1987  Mullis .................... 435/91

OTHER PUBLICATIONS

Kwok and Higuchi, "Avoiding False Positives of PCR", *Nature*, vol. 339, (1989) pp. 237–238.

Saiki et al., "Primer-Directed Enzymatic...", *Science*, vol. 239, (1988), 487–491.

Schaaper et al., *PNAS*, "Infidelity of DNA Synthesis Associated...", vol. 80, pp. 487–491 (1983).

Primary Examiner—Robert A. Wax
Assistant Examiner—Eric Steffe
Attorney, Agent, or Firm—Sterne, Kessler, Goldstein & Fox

[57] ABSTRACT

In the process according to this invention, an amplification procedure is performed on a first sample in which one or more of the four normal ribonucleoside triphosphates (rNTPs) or deoxyribonucleoside triphosphates (dNTPs) is replaced with an exo-sample nucleotide. After amplification, any contaminating amplified product that may be remaining is subjected to a physical, chemical, enzymatic, or biological treatment which renders nucleic acid containing the exo-sample nucleotide substantially unamplifiable. The treatment may be done as a separate step or it may be done in the presence of a second sample containing nucleic acid sequences to be amplified. The amplified nucleic acid sequences derived from the first sample which contaminate the second sample are not further substantially amplified during amplification of nucleic acid sequences of the second sample.

4 Claims, No Drawings

PROCESS FOR CONTROLLING
CONTAMINATION OF NUCLEIC ACID
AMPLIFICATION REACTIONS

BACKGROUND OF THE INVENTION

1. Field of the Invention

The present invention relates to processes which amplify nucleic acid sequences. In particular, the present invention discloses a means for eliminating the products of an execution of a nucleic acid amplification process that contaminate subsequent executions of the amplification process.

2. Description of Related Disclosures

The polymerase chain reaction (PCR) procedure amplifies specific nucleic acid sequences through a series of manipulations including denaturation, annealing of primers, and extension of the primers with DNA polymerase (Mullis KB et al., U.S. Pat. No. 4,683,202, U.S. Pat. No. 4,683,195; Mullis KB, EP 201,184; Erlich H, EP 50,424, EP 84,796, EP 258,017, EP 237,362; Erlich H, U.S. Pat. No. 4,582,788; Saiki R et al., U.S. Pat. No. 4,683,202; Mullis KB et al. (1986) in Cold Spring Harbor Symp. Quant. Biol. 51:263; Saiki R et al. (1985) Science 230:1350; Saiki R et al. (1988) Science 231 487; Loh EY et al. (1988) Science 243:217; etc.). (References cited herein are hereby incorporated by reference.) These steps can be repeated many times, potentially resulting in large amplifications of the number of copies of the original specific sequence. It has been shown that even single molecules of DNA can be amplified to produce hundreds of nanograms of product (Li H et al. (1988) Nature 335:414).

Other known nucleic acid amplification procedures include the transcription-based amplification system of Kwoh D et al. (1989) Proc. Natl. Acad. Sci. USA 86:1173.

"Uracil DNA glycosylase" (UDG), a term of art, refers to an enzyme which cleaves the glycosidic bond between the base uracil and the sugar deoxyribose, only when the monomeric nucleotide dUTP is incorporated into a DNA molecule, resulting in incorporation of a deoxyuridine moiety (Duncan B (1981) in *The Enzymes* 14:565, ed.: Boyer P). The enzyme does not act upon free dUTP, free deoxyuridine, or RNA (Duncan, supra).

A consequence of amplification processes such as PCR is that the amplification products themselves can be substrates for subsequent PCR procedures. Furthermore, because the quantities of the amplification products can be large, the dispersal of even an extremely small fraction of a reaction such as a PCR reaction into the laboratory area potentially can lead to contamination of later attempts to amplify other samples.

The present invention represents an improvement upon in vitro nucleic acid amplification procedures in general by making amplification products distinguishable from naturally occurring DNA. Accordingly, such products are rendered inactive as templates for further amplification prior to the start of the succeeding amplification reaction.

SUMMARY OF THE INVENTION

The present invention involves a process for incorporating an exo-sample nucleotide into DNA or RNA during amplification procedures. The invention eliminates the products of previous amplifications from further amplification by means of a treatment that leaves nucleic acid from the sample unaffected in its ability to be amplified. This treatment greatly reduces a major problem associated with amplification of nucleic acids, namely contamination of starting materials with the end products of previous amplification processes. In other words, the present invention provides a process of discriminating against amplification products, and in favor of nucleic acids normally found in nature, prior to the start of succeeding amplification reactions.

More specifically, the invention relates to in vitro procedures which utilize enzymes to amplify specific nucleic acid sequences. One example of such a procedure is known as the polymerase chain reaction (PCR). A serious limitation of the PCR procedure and other similar procedures is contamination of the laboratory environment with the amplified nucleic acid end products of individual reactions. Such contamination commonly results in amplification not only of authentic nucleic acid which may be present in the sample of interest, but also of the contaminating end products from previous reactions. The present invention provides a process to remove possible contamination of this type, without affecting the desired amplification of authentic nucleic acids.

The present invention involves first performing amplification procedures in which one or more of the four normal ribonucleoside triphosphates (rNTPs) or deoxyribonucleoside triphosphates (dNTPs) is replaced with one or more exo-sample nucleotides that are normally absent from or present very rarely in nucleic acids found in the samples whose amplification is desired. The DNA or RNA produced during such amplification processes can be differentiated from sample nucleic acids. Thus, one can discriminate against nucleic acids produced during amplification processes in favor of sample DNA or RNA prior to or during succeeding amplification processes, such that previously amplified nucleic acid can no longer be amplified, while sample DNA or RNA remains amplifiable.

It is believed that since the invention of the various nucleic acid amplification methods no one has disclosed a means for eliminating contamination of input nucleic acid by the products of previous cycles of amplification.

DETAILED DESCRIPTION OF THE INVENTION

The term "amplifying", as used herein, refers to any in vitro process for increasing the number of copies of a nucleotide sequence or sequences. Nucleic acid amplification results in the incorporation of nucleotides into DNA or RNA.

"Nucleotide" is a term of art that refers to a base-sugar-phosphate combination. Nucleotides are the monomeric units of nucleic acid polymers, i.e. of DNA and RNA. The term includes ribonucleoside triphosphates, such as rATP, rCTP, rGTP, or rUTP, and deoxyribonucleoside triphosphates, such as dATP, dCTP, dGTP, or dTTP.

"Nucleoside" is a term of art referring to a base-sugar combination, i.e. a nucleotide lacking a phosphate moiety. It is recognized in the art that there is a certain inter-changabilty in usage of the terms nucleoside and nucleotide. For example, the nucleotide deoxyuridine triphosphate, dUTP, is a deoxyribonucleoside triphosphate. After incorporation into DNA, it serves as a DNA monomer, formally being deoxyuridylate, i.e. dUMP or deoxyuridine monophosphate. One may say that one incorporates dUTP into DNA even though there is no dUTP moiety in the resultant DNA. Similarly, one may say that one incorporated deoxyuridine into DNA even though that is only a part of the substrate molecule.

The term "exo-sample nucleotide", as used herein, refers to a nucleotide which is generally not found in the sample to be amplified. For most DNA samples, deoxyuridine is an example of an exo-sample nucleotide. Although the triphosphate form of deoxyuridine, dUTP, is present in living organisms as a metabolic intermediate, it is rarely incorporated into DNA. When dUTP is accidentally incorporated into DNA, the resulting deoxyuridine is promptly removed in vivo by normal processes, e.g. processes involving the enzyme UDG. Thus, deoxyuridine occurs rarely or never in natural DNA. It is recognized that some organisms may naturally incorporate deoxyuridine into DNA. For nucleic acid samples of those organisms, deoxyuridine would not be considered an exo-sample nucleotide. The presence of deoxyuridine, or any other exo-sample nucleotide, may be determined readily using methods well known to the art. Other exo-sample nucleotides may be envisioned. Numerous DNA glycosylases are known to the art. An exo-sample nucleotide which may be incorporated into DNA during an amplification and a DNA glycosylase that acts on it may be used in this invention. Similarly, bromodeoxyuridine (BdUR) is well known in the art to be incorporated into DNA. DNA containing BdUR may be degraded on exposure to light under appropriate conditions.

The term "incorporating" refers to becoming part of a nucleic acid polymer.

The term "terminating" refers herein to causing a treatment to stop. The term includes means for both permanent and conditional stoppages. For example, if the treatment is enzymatic, both permanent heat denaturation and lack of enzymatic activity due to a temperature outside the enzyme s active range would fall within the scope of this term.

In the process according to this invention, an amplification procedure is performed on a first sample in which one or more of the four normal ribonucleoside triphosphates (rNTPs) or deoxyribonucleoside triphosphates (dNTPs) is replaced with an exo-sample nucleotide. After amplification, any contaminating amplified product that may be remaining is subjected to a physical, chemical, enzymatic, or biological treatment which renders nucleic acid containing the exo-sample nucleotide substantially unamplifiable. The treatment may be done as a separate step, or preferably, may be done in the presence of a second sample containing nucleic acid sequences to be amplified. The amplified nucleic acid sequences derived from the first sample which contaminate the second sample are not further substantially amplified during amplification of nucleic acid sequences of the second sample.

The deoxyribonucleoside triphosphate dUTP exemplifies an exo-sample nucleotide which may be conveniently incorporated into an enzymatic DNA amplification procedure, exemplified herein by PCR, thereby resulting in deoxyuridine-containing DNA. The DNA products of such a reaction will normally contain many uracil bases. Discrimination between natural DNA and the resultant, deoxyuridine-containing products of amplification procedures may be obtained with the enzyme uracil DNA glycosylase (UDG). Treatment of DNA containing uracil bases with uracil DNA glycosylase results in cleavage of the glycosidic bond between the deoxyribose of the DNA sugar-phosphate backbone and the uracil base. The loss of the uracil creates an apyrimidinic site in the DNA, which blocks DNA polymerase from using the DNA strand as a template for the synthesis of a complementary DNA strand (Schaaper R et al. (1983) Proc. Natl. Acad. Sci. USA 80:487). The presence of substantial numbers of apyrimidinic sites in each DNA target molecule interferes with amplification procedures which use DNA polymerase to synthesize copies of target DNA.

As exemplified herein, the basic amplification protocol is the well known PCR method. PCR was modified in three ways: (1) dUTP was substituted for dTTP; (2) UDG was added to the initial PCR reaction mixture; and (3) an initial incubation period was added to allow UDG to destroy contaminating products of prior PCR reactions. The UDG itself was either permanently inactivated by high temperature in the first PCR cycle or was not active at the high temperatures used with Taq polymerase in the currently preferred PCR protocol. This inactivation prevents UDG from destroying newly-synthesized PCR products. Nucleic acid amplification protocols that do not eliminate UDG activity usually will require an extra UDG-inactivation step.

While termination of the physical, chemical, enzymatic, or biological treatment that renders nucleic acid containing the exo-sample nucleotide resistant to the amplification process is preferred (as exemplified herein, heat inactivation of UDG), the invention also includes embodiments lacking a termination step. For example, one might use amounts of enzyme and durations of treatment high enough to eliminate expected contamination of starting materials but insufficient to keep up with the rate of amplification. In other words, a treatment might be able to destroy contaminating nucleic acid but an amplification process might still be able to produce new nucleic acid faster than the treatment could destroy the newly synthesized nucleic acid.

Variations on the herein disclosed invention may also be envisioned. For example, the amplification may be done without an exo-sample nucleotide, i.e., using normal nucleotides. A normal nucleotide in the amplified DNA is then converted into an exo-sample nucleotide. The converted DNA can then be removed from any samples which it later contaminates. An example would be the conversion of neighboring pyrimidine residues, especially thymidine, into pyrimidine dimers (thymidine dimers), which make DNA unsuitable as a template. Thymidine dimers can also be removed by enzymes such as exonuclease VII and recBC.

EXAMPLE

A polymerase chain reaction (PCR) was performed to amplify a region of the human papilloma virus type 16 (HPV 16) DNA (Durst M et al. (1983) Proc. Natl. Acad. Sci. USA 80:3812). The sequences of the primers used were 5'GGTCGATGTATGTCTTGTTG3' and 5'GTCTACGTGTGTGCTTTGTAC3'.

HPV 16 DNA was excised from a full length plasmid clone, pT7HPV16 (for the purposes of this invention, equivalent to the pUC8 plasmids described by Seedoff K et al. (1985) Virol. 145:181) with the restriction enzyme BamH 1. The linear DNA (10 picograms) was added to PCR reactions containing 50 microliters of 25 mM Tris HCl pH 8.3, 5 mM $MgCl_2$, 50 mM NaCl, 0.01% gelatin, 0.05% W1 polyoxyethylene ether detergent (Sigma), 0.2 mM each dATP, dGTP, dCTP, 0.2 mM either dUTP or dTTP, 1 micromolar of each primer, and 12.5 units of thermostable DNA polymerase from *Thermus aquaticus* (Cetus/Perkin-Elmer). The reactions were amplified in a thermal cylcer (Cetus/Perkin-Elmer) using the following temperature profile: 5 minutes at 94° C., then 30 cycles of 1 minute at 94° C. (denaturation), two minutes at 55° C. (annealing), and 3 minutes at 72° C. (primer extension). After completion of the temperature cycles, a final extension of 10 minutes at 72° C. was done. Amplification of the 284 base pair HPV 16 DNA fragment was confirmed by agarose/ethidium bromide gel electrophoresis (Maniatis T et al. (1982) *Molecular Cloning*, Cold Spring Harbor Laboratory) of the PCR reaction products (5 microliters of each reaction per lane). All reactions showed substantial amplification. Negative control reactions to which no HPV 16 DNA was added did not produce any DNA products.

The concentration of the PCR amplification products was estimated from the agarose gel. New PCR reactions were contaminated with ten femtogram quantities of the amplification products that contained either deoxythymidine, resulting from incorporation of dTTP, or deoxyuridine, from dUTP-containing reactions. Positive control reactions contained 10 picograms of linear HPV 16 DNA. Negative control reactions did not receive any target DNA. The new PCR reactions contained dUTP instead of dTTP, and either 5 nanograms of UDG (Van de Sande H, University of Calgary; also available from Duncan Laboratories, 19 E. Central Ave., Paoli, PA 19301 USA) or no UDG. All reactions were incubated for 15 minutes at 37° C. to allow the UDG to act on deoxyuridine-containing DNA, and then were taken through the same thermal cycling protocol as above. Aliquots of each reaction were analyzed by agarose/ethidium bromide gel electrophoresis.

The agarose gel analysis showed that without UDG treatment the deoxyuridine-containing PCR products could be re-amplified to give a DNA product indistinguishable in size, as evidenced by gel electrophoresis, from the products obtained by amplifying the normal HPV 16 DNA. Reactions in which the deoxyuridine-containing DNA was incubated with UDG prior to PCR did not give any visible products on the agarose gel. PCR amplification products that contained deoxythymidine were successfully amplified whether or not they had been incubated with UDG. This experiment showed that UDG substantially abolished amplification of PCR products containing deoxyuridine, but had no substantial effect on the amplification of DNA containing deoxythymidine.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

What is claimed is:

1. A method for controlling contamination in sequential nucleic acid amplification processes comprising first and second nucleic acid amplification processes to amplify nucleic acid sequences in a first and a second sample, respectively, which comprises:

carrying out said first nucleic acid amplification process on said nucleic acid sequence in said first sample in the presence of deoxyuridine triphosphate, to thereby generate a deoxyuracil-containing product of amplification; and treating said deoxyuracil-containing product of amplification with uracil DNA glycosylase prior to carrying out said second amplification process on said nucleic acid sequence in said second sample.

2. The process of claim 1 wherein said nucleic acid sequences in said first and second samples have two separate complementary strands each, wherein said first nucleic acid amplification process on said first sample comprises:

(1) treating said strands with two oligonucleotide primers, for each different specific sequence being amplified, under conditions such that for each different sequence being amplified, an extension product of each primer is synthesized which is complementary to each nucleic acid strand and which incorporates deoxyuridine, wherein said primers are selected so as to be sufficiently complementary to different strands of each specific sequence to hybridize therewith, such that the extension product synthesized from one primer, when it is separated from its complement, can serve as a template for synthesis of the extension product of the other primer;

(2) separating the primer extension products from the templates on which they are synthesized to produce single-stranded molecules;

(3) treating said single-stranded molecules generated from step (2) with the primers of step (1) under conditions that a primer extension product is synthesized using each of the single strands produced in step (2) as a template;

(4) repeating steps (1) through (3) at least once, thereby amplifying said specific nucleic acid sequence contained in said first sample;

and wherein said second nucleic acid amplification process on said second sample comprises (5) treating said second sample with uracil DNA glycosylase; and (6) repeating steps (1) through (3) on said second sample at least once, thereby amplifying the nucleic acid sequence contained in said second sample.

3. The process of claim 1 wherein, after treating said deoxyuracil-containing product with uracil DNA glycosylase, and prior to carrying out said second amplification process, the second sample is heated so as to terminate the action of said uracil DNA glycosylase.

4. The process of claim 2 wherein, after said step (5), the process comprises:

(7) heating said sample so as to terminate the action of said uracil DNA glycosylase.

* * * * *